United States Patent
Ahn et al.

(10) Patent No.: US 10,331,954 B2
(45) Date of Patent: Jun. 25, 2019

(54) METHOD FOR CONTROLLING GAS AND ELECTRONIC DEVICE THEREOF

(71) Applicant: SAMSUNG ELECTRONICS CO., LTD., Suwon-si, Gyeonggi-do (KR)

(72) Inventors: Jihyun Ahn, Seoul (KR); Hyunkyoung Kim, Seoul (KR); Daeun Park, Seoul (KR); Jung-Sik Park, Suwon-si (KR); Hyung-Woo Shin, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 164 days.

(21) Appl. No.: 15/146,046

(22) Filed: May 4, 2016

(65) Prior Publication Data
US 2016/0328612 A1   Nov. 10, 2016

(30) Foreign Application Priority Data
May 6, 2015  (KR) .................. 10-2015-0063192

(51) Int. Cl.
*G06K 9/00* (2006.01)
*G01N 33/00* (2006.01)
(Continued)

(52) U.S. Cl.
CPC ....... *G06K 9/00671* (2013.01); *G01N 33/004* (2013.01); *G01N 33/0036* (2013.01);
(Continued)

(58) Field of Classification Search
CPC ............ G06K 9/00671; H04N 5/23293; G06T 7/0002; G01N 33/0036; G01N 33/004; G01N 33/0073
See application file for complete search history.

(56) References Cited

U.S. PATENT DOCUMENTS 5,817,921 A * 10/1998  Tom .................. G01N 29/036
                                                       73/24.01
2003/0034454 A1 * 2/2003  Nomura .................. G01J 3/42
                                                       250/339.13
(Continued)

FOREIGN PATENT DOCUMENTS

CN        201508453       6/2010
CN        102331482       1/2012
(Continued)

OTHER PUBLICATIONS

Office Action dated Sep. 14, 2017 in counterpart Chinese Patent Application No. CN201610296641.5.
(Continued)

*Primary Examiner* — Tat C Chio
(74) *Attorney, Agent, or Firm* — Nixon & Vanderhye P.C.

(57) ABSTRACT

An electronic device that may collect gas and provide information associated with gas, and a operating method thereof are disclosed. The electronic device may include: a gas sensor that detects gas; a processing unit that analyzes the components of detected gases so as to determine whether abnormal gas is included; and a display unit that displays the analyzed gases on a screen, and displays abnormal gas to be emphasized. A method of operating the electronic device may include: detecting gases through the gas sensor; analyzing the detected gases and analyzing whether abnormal gases exist; displaying the analyzed gases on a screen and displaying abnormal gases to be emphasized.

18 Claims, 12 Drawing Sheets

(51) Int. Cl.
*G06T 7/00* (2017.01)
*H04N 5/232* (2006.01)

(52) U.S. Cl.
CPC ....... *G01N 33/0073* (2013.01); *G06T 7/0002* (2013.01); *H04N 5/23293* (2013.01)

(56) References Cited

U.S. PATENT DOCUMENTS

| | | | | |
|---|---|---|---|---|
| 2009/0018712 | A1* | 1/2009 | Duncan | G09B 19/167 |
| | | | | 701/2 |
| 2012/0166022 | A1 | 6/2012 | Kwon et al. | |
| 2014/0208829 | A1 | 7/2014 | Lechner et al. | |
| 2014/0225918 | A1* | 8/2014 | Mittal | G06F 3/017 |
| | | | | 345/633 |
| 2014/0375463 | A1 | 12/2014 | Duric | |
| 2016/0110816 | A1* | 4/2016 | Cardin | G06Q 40/08 |
| | | | | 705/4 |
| 2016/0140829 | A1* | 5/2016 | Romanoff | G06Q 10/06 |
| | | | | 340/540 |

FOREIGN PATENT DOCUMENTS

| | | |
|---|---|---|
| CN | 103312773 | 9/2013 |
| CN | 203385707 | 1/2014 |
| CN | 203799032 | 8/2014 |
| CN | 104571142 | 4/2015 |
| CN | 105191714 | 12/2015 |
| EP | 0 317 299 | 5/1989 |
| KR | 10-2006-0060235 | 6/2006 |
| KR | 10-2007-0074858 | 7/2007 |
| KR | 10-2013-0078235 | 7/2013 |
| WO | WO 2006/059815 | 6/2006 |

OTHER PUBLICATIONS

Extended Search Report dated Sep. 20, 2016 in counterpart European Application No. 16168268.7.
Office Action and Translation for CN Application No. 201610296641.5 dated Feb. 14, 2018.
European Office Action for EP Application No. 16168268.7 dated Mar. 26, 2019.
"Airborne Visualization and Quantification of Discrete Methane Sources in the Environment"; Tratt et al., Remote Sensing of Environment 154 (2014) pp. 74-78.

* cited by examiner

METHOD FOR CONTROLLING GAS AND ELECTRONIC DEVICE THEREOF

CROSS-REFERENCE TO RELATED APPLICATION

This application is based on and claims priority under 35 U.S.C. § 119 to Korean Application Serial No. 10-2015-0063192, which was filed in the Korean Intellectual Property Office on May 6, 2015, the contents of which are incorporated by reference herein in its entirety.

TECHNICAL FIELD

The present disclosure relates to an electronic device that may collect gas and provide information, and to a controlling method thereof.

BACKGROUND

As digital technologies have developed recently, various types of electronic devices have become widely utilized, such as a smart phone, a tablet Personal Computer (PC), a Personal Digital Assistant (PDA), an electronic organizer, a notebook, a wearable device, or the like. The electronic devices have reached a level of mobile convergence that includes the functions of other devices. For example, an electronic device may provide: a call function, such as a voice call, a video call, or the like; a message transmit/receive function, such as a Short Message Service (SMS)/Multimedia Message Service (MMS), an e-mail, or the like; an electronic organizer function; a photographing function; a broadcasting program reproduction function; a video reproduction function; a music reproduction function; an Internet function; a messenger function; a game function; a social network service (SNS) function, or the like.

The electronic device may display gas information. A conventional art that provides gas information through an electronic device, provides numerical values associated with O3, NO, CO, SO2, or the like (yellow dust, ozone, and fine dust) in a corresponding region by using official information issued from the Meteorological Administration or the like, or may provide numerical values or a warning when abnormal gas, such as smoke (CO), a volatile organic compound (VOC), or the like, is detected through a dedicated device.

SUMMARY

As described above, in the case of the method that uses the information that is publicly known by the Meteorological Administration or the like, the location where gas is measured and the location of a user are different, and thus, the method may not be useful. Also, the conventional gas measuring method merely displays a gas measurement result. Therefore, the conventional gas measuring method may be limited in terms of providing a warning, and also may not provide the cause of the abnormal gas.

According to various embodiments of the present disclosure, there is provided a method and apparatus which may enable an electronic device to detect gas and to efficiently display the components of the detected gas.

According to various embodiments of the present disclosure, there is provided a method and apparatus that may collect and analyze gas components associated with an image that is obtained by a camera, and may display an analyzed result to be matched to the image.

According to various embodiments of the present disclosure, there is provided an electronic device, including: a gas sensor that detects components of air; a camera; a processor configured to analyze the detected components of air; and a display unit that displays the analyzed components of air on a screen of the electronic device.

According to various embodiments of the present disclosure, there is provided an operation method of an electronic device, including: driving a gas sensor and a camera; detecting components of air using the gas sensor; analyzing the detected components of air; and displaying the analyzed components of air on a screen of the electronic device.

According to various embodiments of the present disclosure, an electronic device and an operation method thereof may smoothly measure gas, an object that causes the generation of gas, information associated with the gas, or a combination thereof, by using a gas sensor, a camera, or a combination thereof. Also, the electronic device and the operation method thereof may display a component ratio of the measured gases on a screen, and/or may display abnormal gas components or harmful gas components out of the detected gases to be emphasized. Also, according to various embodiments of the present disclosure, an electronic device and an operation method thereof may obtain, through a camera, an image of a target to be measured, may measure the components of gas associated with the obtained image, and may display the measured gases to be matched to the image displayed on the screen.

BRIEF DESCRIPTION OF THE DRAWINGS

The above and other aspects, features, and advantages of the present disclosure will be more apparent from the following detailed description, taken in conjunction with the accompanying drawings, in which like reference numerals refer to like elements, and wherein.

DETAILED DESCRIPTION

Figure 1:
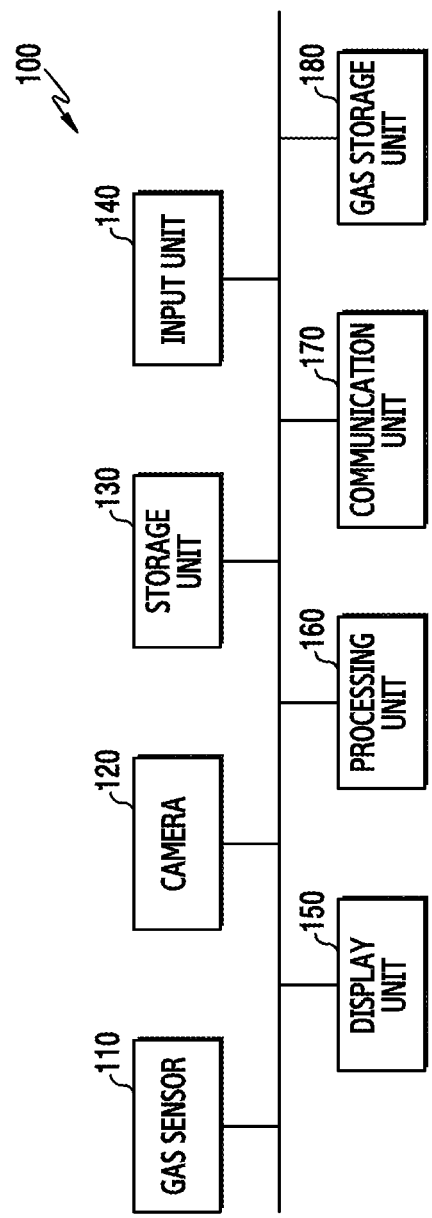
FIG. 1 is a block diagram illustrating an example electronic device that processes gas according to an embodiment of the present disclosure.

Hereinafter, various example embodiments of the present disclosure will be described with reference to the accompanying drawings. However, it should be understood that there is no intent to limit the present disclosure to the particular forms disclosed herein; rather, the present disclosure should be construed to cover various modifications, equivalents, and/or alternatives of embodiments of the present disclosure. In the description of the drawings, similar reference numerals may be used to designate similar elements.

The terms used in the present disclosure are only used to describe example embodiments, and are not intended to limit the present disclosure. As used herein, singular forms may include plural forms as well unless the context clearly indicates otherwise. Unless defined otherwise, all terms used herein, including technical and scientific terms, have the same meaning as those commonly understood by a person skilled in the art to which the present disclosure pertains. Such terms as those defined in a generally used dictionary may be interpreted to have the meanings equal to the contextual meanings in the relevant field of art, and are not to be interpreted to have ideal or excessively formal meanings unless clearly defined in the present disclosure. In some cases, even the term defined in the present disclosure should not be interpreted to exclude embodiments of the present disclosure.

An electronic device according to various embodiments of the present disclosure may include at least one of, for example, a smart phone, a tablet Personal Computer (PC), a mobile phone, a video phone, an electronic book reader (e-book reader), a desktop PC, a laptop PC, a netbook computer, a workstation, a server, a Personal Digital Assistant (PDA), a Portable Multimedia Player (PMP), a MPEG-1 audio layer-3 (MP3) player, a mobile medical device, a camera, and a wearable device, or the like. According to various embodiments, the wearable device may include at least one of an accessory type (e.g., a watch, a ring, a bracelet, an anklet, a necklace, a glasses, a contact lens, or a Head-Mounted Device (HMD)), a fabric or clothing integrated type (e.g., an electronic clothing), a body-mounted type (e.g., a skin pad, or tattoo), and a bio-implantable type (e.g., an implantable circuit), or the like.

Hereinafter, various embodiments of the present disclosure will be described from the perspective of hardware. However, various embodiments of the present disclosure include a technology that uses both hardware and software and thus, the various embodiments of the present disclosure may not exclude the perspective of software.

FIG. 1 is a block diagram illustrating an example electronic device that processes gas according to an embodiment of the present disclosure.

Referring to FIG. 1, an electronic device 100 may include a gas sensor 110, a camera 120, a storage unit 130, an input unit (e.g., including input circuitry) 140, a display unit (e.g., including a display panel) 150, a processing unit (e.g., including processing circuitry) 160, a communication unit (e.g., including communication circuitry) 170, and/or a gas storage unit 180.

The term gas, as used herein, may include the components of air, gases, and the like. Also, gas may be used interchangeably with the components of air, gases, or the like.

The gas sensor 110 may indicate a set of at least one gas sensor. The gas sensor 110 may be located in the electronic device by being distributed densely or sparsely. The gas sensor 110 may detect gases existing around the electronic device. Particularly, the gas sensor 110 may collect gases existing around the electronic device, and may convert the collected gases into electrical signals. The gas sensor 110 may be a semi-conductor sensor. In this instance, the types of collected gases may be determined based on an oxidation-reduction reaction of the collected gases. The entire gas sensor 110 may operate at a time, as needed, and may detect gas existing around the electronic device. Also, some or the entirety of the gas sensor 110 may operate, as occasion demands, and may detect gas existing in a predetermined direction around the electronic device. Also, each gas sensor 110 may independently aim at a predetermined direction, as needed, and may detect gas. When multiple gas sensors 110 are included in the electronic device, each gas sensor 110 may recognize a direction based on a difference in gas recognition times between sensors.

The camera 120 may indicate a set of at least one camera. The camera 120 may be located in the electronic device by being distributed densely or sparsely. Also, the camera 120 may be located to be adjacent to the gas sensor 110. This is to enable a user to provide a visual reference using the camera 120 according to various embodiments of the present disclosure.

The storage unit 130 may indicate a set of at least one memory. The storage unit 130 may store an electrical signal converted by the gas sensor 110. The storage unit 130 may store reference data to be compared with the detected gas when needed. The reference data may include reference atmospheric gas information, reference gas information associated with an object, information associated with an object indicated by a character, information associated with a combination thereof, or the like. The storage unit 130 may store instructions, programs, or the like, which are required by a module that forms the processing unit 160.

The input unit 140 may include circuitry configured to detect an input through an electronic device. The input unit 140 may be a touch panel. The input unit 140 may detect a touch or a hovering input provided by a finger and a pen. The input unit 140 may generate inputs associated with detecting and processing gas according to various embodiments of the present disclosure.

The displaying unit 150 may include a display panel and display a result processed in the electronic device. The displaying unit 150 may be a Liquid Crystal Display (LCD) or an Organic Light Emitting Diodes (OLED), or the like. The displaying unit 150 may display detected gases based on a component radio, and may display abnormal gases that may be included in the detected gases, to be emphasized. Also, the displaying unit 150 may display the detected gases included in an image obtained by the camera 120.

The input unit 140 and the display unit 150 may be formed as an integral touch screen.

The processing unit 160 may include processing circuitry configured to perform a function of analyzing gas that is detected by the gas sensor 110, a function of controlling the direction of the gas sensor 110 and/or the camera 120, a function of recognizing an object photographed by the camera 120, a function of recognizing a character photographed by the camera 120, a function of controlling the expression displayed through the displaying unit 150, and the like. The processing unit 160 may be included in the electronic device in the form of a single chip. Also, the processing unit 160 is separated, and each may be coupled with internal components of the electronic device (e.g., the gas sensor 110, the camera 120, and the like), as needed.

For example, when the gas sensor 110 detects gases existing around the electronic device, the processing unit 160 may analyze the detected gases and may determine a component ratio of the gases. Also, the processing unit 160 may determine abnormal gas based on a result of the analysis. The abnormal gas may include a meaning indicating harmful gas. Also, the abnormal gas may include a meaning that is not harmful indicates gas that on its own, but may become harmful to the human body when having a relationship with other gases existing nearby. Also, the abnormal gas may include a meaning that indicates gas that is not harmful on its own, but may cause a problem when a component ratio thereof occupies an excessively large portion or excessively small portion.

The processing unit 160 may include a function of processing the analyzed gases. The processing unit 160 may provide a warning in association with a harmful state or a dangerous state of an environment where the electronic device is located, based on types of detected gases and a result of analyzing a component ratio. The gas may be classified as a combustible gas (e.g., hydrogen, ammonia, propane, butane, acetylene, and the like); a combustion-supporting gas (e.g., oxygen, chlorine, and the like); a noncombustible gas; and the like. The processing unit 160 may analyze the detected gases, and may provide a warning indicating that the environment of a user is in an abnormal state when a combustible gas is detected. Also, when the combustible gas is detected and the component ratio of the detected combustible gas is high, the processing unit 160 may provide a warning indicating that the environment of the user is currently dangerous. Also, when toxic gas which is harmful to the human body (e.g., chlorine, carbon monoxide, sulfurous acid gas, ammonia, ethylene oxide, and the like), the processing unit 160 may provide a warning indicating that harmful gas exists in the environment of the user. When the abnormal state, dangerous state, and harmful gas detection state are recognized, the processing unit 160 may provide a warning associated with a corresponding state in various forms (e.g., a visual and/or auditory format) in order to enable a user to recognize the same.

The processing unit 160 may receive an image obtained by the camera 120, and may process the image.

The processing unit 160 may analyze the gases that are detected by a user through the gas sensor 110, and may execute a function of displaying the same in the display unit 150. In this instance, a method of displaying the components of the gas may include: a method of displaying an amount of gas through characters (a component ratio, % ratio, mole ratio, or the like); a method of visually displaying a relative amount of gas through figures or the like; a displaying method using a combination thereof; and the like. The processing unit 160 may determine whether abnormal gas exists. When the abnormal gas exists, the processing unit 160 may enable the existence of the abnormal gas to be displayed and emphasized in the display unit 150, irrespective of the amount of abnormal gas detected. When the information is expressed by characters, a method of displaying the information to be emphasized may include expressing a name in bold or enlarging the name, when compared to the others. Also, when the information is expressed using figures or the like, the method of displaying the information to be emphasized may include visually enlarging a figure or expressing the figure by a distinguishing color, when compared to the others. Also, the method of displaying information to be emphasized may include expressing the information in a format that is different from other gases. Also, the method of displaying information to be emphasized may include displaying a warning message, providing an alert, or the like, in addition to displaying the existence of abnormal gas to be emphasized. That is, the method of displaying the information to be emphasized may include schemes that are generally used for attracting attention.

When information associated with the gas detected by the gas sensor 110 needs to be obtained, the communication unit 170 may be used for the communication with an external server. Also, when information associated with the image that is recognized by the camera 120 needs to be obtained, the communication unit 170 may be used for the communication with an external server.

The gas storage unit 180 may be a device that is capable of storing gas that is detected by the gas sensor 110. Also, the gas storage unit 180 may be charged with a predetermined gas provided from the outside. The gas storage unit 180 may include a gas processing unit that processes whether to store gas, an electric signal storage unit that stores an electrical signal associated with detected gas, a cartridge formed of gas components that may reproduce sprayed gas, a spraying unit that sprays gas, or a combination thereof. The gas storage unit 180 may include a function that reproduces and sprays detected gas through the cartridge that is contained inside or outside the gas storage unit 180. The gas storage unit 180 may be located inside the electronic device, or may be located outside the electronic device as an independent entity. Also, the gas storage unit 180 may be located to be detachable from the electronic device.

Figure 2:
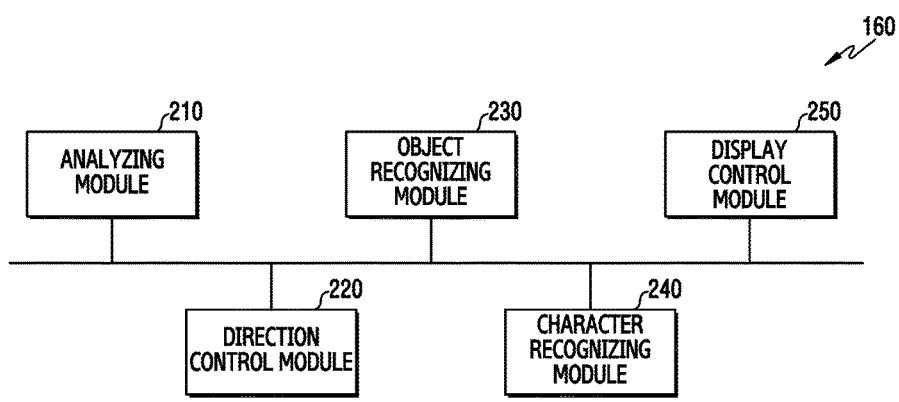
FIG. 2 is a block diagram illustrating an example processing unit according to various embodiments of the present disclosure.

FIG. 2 is a block diagram illustrating a processing unit according to various embodiments of the present disclosure. Particularly, FIG. 2 illustrates a configuration of modules inside the processing unit of FIG. 1.

Referring to FIG. 2, the processing unit 160 may include an analyzing module 210, a direction control module 220, an object recognizing module 230, a character recognizing module 240, and/or a display control module 250. As used herein, the term module may refer to processing circuitry of the processing unit configured to perform a particular function. The processing circuitry may, for example, be configured to perform the particular function using software.

The analyzing module 210 may perform a function of analyzing gases detected by the gas sensor 110. Particularly, the analyzing module 210 may include a function of analyzing the types of detected gas, and a component radio of detected gases. Also, when the gas sensor 110 and the camera 120 interoperate, the analyzing module 210 may include a function of analyzing detected gases based on image information obtained by the camera 120.

For example, when the gas sensor 110 detects atmospheric gases, the analyzing module 210 may analyze that the atmospheric gases includes nitrogen, oxygen, and other gases (carbon dioxide, hydrogen, neon, helium, krypton, xenon, methane, ozone, and the like). Also, the analyzing module 210 may execute an analysis showing that the component ratio of the atmospheric gases is 78% nitrogen, 21% oxygen, and 1% other gases (carbon dioxide, hydrogen, neon, helium, krypton, xenon, methane, ozone, and the like).

Also, the analyzing module 210 may determine whether abnormal gas exists based on the analyzed types and component ratio of the gases. Here, the abnormal gas may indicate harmful gas, and may indicate gas of which the ratio is excessively large or small, when compared to the ordinary case. Also, the abnormal gas may be defined in advance by a user. For example, when gas that is harmful to the human body, such as chlorine, carbon monoxide, sulfurous acid gas, and the like, is included in the gases detected by the gas sensor 110, the analyzing module 210 may determine that the corresponding gas is abnormal gas. Also, for example, when the component ratio of oxygen in the gases detected by the gas sensor 110 is measured to be excessively large (50%) or small (5%), the analyzing module 210 may determine oxygen as abnormal gas. Here, the abnormal gas may include harmful gas (direct harmful gas and gas that may cause a harmful situation by combining with another gas) and dangerous gas (direct dangerous gas and gas that may cause a dangerous situation by combining with another gas). When it is a situation in which gases combine and cause a harmful or dangerous situation, the analyzing module 210 may execute an analysis so that the names (component ratio and the like) of all of the corresponding gases may be emphasized.

The direction control module 220 may include a function of controlling the direction of the gas sensor 110 and/or the camera 120. The gas sensor 110 may be formed of one sensor or a set of two or more sensors. When the gas sensor 110 is formed of two or more sensors, each sensor may be mounted on different locations of the electronic device (e.g., a front side/back side and/or an upper lateral side/lower lateral side). Also, the gas sensor 110 may be installed in a form that is capable of changing a collecting direction. Therefore, when a plurality of gas sensors are included, the direction control module 220 may drive a gas sensor that is mounted in the location (direction) identical to the camera 120. Also, when the gas sensor is capable of aiming at a direction, the direction control module 220 may control the gas sensor to aim at a driving direction of the camera. Hereinafter, descriptions will be provided by assuming that the gas sensor is capable of changing a direction.

Particularly, when a user desires to detect gas existing in a predetermined direction, the direction control module 220 may control a photographing direction of the camera 120. Also, the direction control module 220 may control the direction of the gas sensor to correspond to an image obtained by the camera 120. For example, when the gas sensor 110 is a directional gas sensor, the direction control module 220 may control the gas sensor 110 to aim at a location to detect gas.

The object recognizing module 230 may recognize objects that are formed or included in an image photographed by the camera 120. Accordingly, the analyzing module 210 may extract, from the detected gases, gases associated with the object recognized through the object recognizing module 230.

The character recognizing module 240 may recognize characters that are formed or included in an image photographed by the camera 120. Accordingly, the analyzing module 210 may extract, from the detected gases, gases associated with the characters recognized through the character recognizing module 240.

The display control module 250 may execute a control to display, in the displaying unit 150, the gases analyzed by the analyzing module 210 and related information. The display control module 250 may execute a control to display, in the displaying unit 150, the analyzed gases based on a corresponding ratio. Also, when at least one abnormal gas is included in the analyzed gases, the display control module 250 may execute a control to display, in the displaying unit 150, the corresponding abnormal gas to be emphasized In this instance, the display control module 250 may execute a control, so that the name or ratio of the abnormal gas may be displayed to be emphasized. Also, the display control module 250 may execute a control to display the analyzed gas in an image obtained by the camera. That is, a user of the electronic device may execute a control using the display control module 250, so that the information associated with the detection of gas may be efficiently displayed through the displaying unit 150.

The electronic device may have a configuration for detecting gas, a configuration for processing a decision, and a configuration for displaying a result. The configuration of detecting gas may be the gas sensor 110 or the camera 120. In this instance, when the gas sensor 110 is driven by interoperating with the camera 120, the processing unit 160 may detect gas existing in a photographing direction (location) of the camera 120, through the gas sensor 110. Also, the processing unit 160 may recognize an object and/or a character of a subject that is photographed by the camera 120 (Optical Object Recognition (OOR) and/or Optical Character Recognition (OCR)), and may collect additional information associated with the detected gas.

The configuration of processing a decision may be the processing unit 160, and may be formed of a processor. The configuration of processing a decision may recognize all of the gas components detected by the gas sensor 110 from the air, and a space, an object, and a label included in an image photographed by the camera 120 (a preview image, a still image, a moving image, and the like), and also, may extract a factor of a common denominator from the storage unit 130 included in the electronic device and/or an external server (an accumulated-information server) using the communication unit 170.

The configuration of processing a result may be the input unit 140, the displaying unit 150, the gas storage unit 180, and the like. The configuration of processing the result may display an image (e.g., Augmented Reality (AR) of a preview image) photographed by the camera 120 under the control of the configuration of processing a decision, and may provide some or the entirety of the result as text. In this instance, the displayed information may include information extracted from an Internet search result and the like. Also, the configuration of displaying a result may spray and share gas (gas detected through the electronic device in a previous step) stored in the gas storage unit 180 through an external accessory, under the control of the configuration of processing a decision.

The electronic device configured as described above may perform the following operations.

First, the electronic device may collect gas by driving the gas sensor 110 and the camera 120 to interoperate with each other. The gas sensor 110 may be capable of controlling a direction (deforming), and the electronic device may recognize a direction based on resolution. When the electronic device drives the camera 120 and the gas sensor 110 to interoperate with each other, the electronic device sets a collecting direction of the gas sensor 110 to a location that is shown through a preview image of the camera 120 (e.g., controls the collecting direction of the gas sensor 110 to aim at a photographing direction of the camera 120), and may collect gas existing in the corresponding direction through the gas sensor 110. In this instance, collecting the gas may be performed by the electronic device, either automatically or manually. For example, when a user operates the camera 120 through a predetermined gesture (e.g., when a user raises or lowers the electronic device by predetermined degrees (90 degrees or the like), the electronic device may automatically operate the gas sensor 110 so as to collect gas. Also, when an input of a set button or the like is provided, the electronic device may operate the gas sensor 110, and may collect (manually collect) gas. The electronic device may analyze the components of the gas collected by the gas sensor 110, and may determine a component ratio (percentage) of the existing gases. The electronic device may display a result of the analysis in a photographed image (e.g., a preview image) of the camera 120 in a size based on corresponding percentages (%), in the display unit 150 as a real-time AR. Also, when abnormal gas (e.g., harmful gas) exists, the electronic device may display a warning (emphasis, for example, a different color, a different size, and the like) in the display unit 150. The abnormal gas may be displayed as a camera image that is displayed in the displaying unit 150. A user may find out or remove a causative substance by determining a space or a product captured by the camera 120 through the displayed camera image.

Second, when the electronic device drives the gas sensor 110 and the camera 120 to interoperate with each other, the electronic device may recognize an object photographed by the camera 120 (Optical Object Recognition (OOR)), and may process detected gas. The gas sensor 110 may collect gas existing in the location where the sensor aims at, and the camera may photograph a subject located in the place (location) where the gas is measured. The electronic device may recognize an object (e.g., a bed, a gas range, and the like) in the image photographed by the camera 120, and may collect additional information. When abnormal gas is included in the detected gas, the electronic device may provide a warning by displaying the abnormal gas to be emphasized in a corresponding object, and may derive the user to remove a causative substance. Also, the electronic device may spray or share a sample of a detected scent through an accessory.

Third, when the electronic device drives the gas sensor 110 and the camera 120 to interoperate with each other, the electronic device may recognize characters (Optical Character Recognition (OCR)) and may process detected gas. The gas sensor 110 may measure gas existing in the location where the sensor aims at, and the camera 120 may photograph a subject located in the place (location) where the gas is measured. The electronic device may recognize a character of an image photographed by the camera 120, and may collect additional information. The electronic device may provide information included in a server that stores character information (e.g., a logo, label information, and the like). Also, the electronic device may spray or share a sample of the collected scent through an accessory.

As described above, an electronic device according to various embodiments of the present disclosure, may include the gas sensor 110 that is capable of detecting the components of air, the camera 120 that is capable of providing a screen, the processing unit 160 that is capable of analyzing the detected components of air, and the displaying unit 150 that is capable of displaying the analyzed components of air on the screen in real time.

The processing unit 160 may be capable of analyzing a ratio of the detected components of air, and the displaying unit 150 may display the analyzed components of air in a size based on a corresponding ratio. Here, the components of air may indicate the same meaning as gases or gas. For example, the components of air may be oxygen ($O_2$), nitrogen ($N_2$), carbon dioxide ($CO_2$), sulfurous acid gas ($SO_2$), carbon monoxide (CO), and the like.

Also, the processing unit 160 may analyze whether an abnormal gas component exists in the analyzed components of air. Here, the abnormal gas may be harmful gas, explosive dangerous gas, gas of which a component ratio is higher than an average value, and the like. For example, the abnormal gas may be sulfurous acid gas ($SO_2$), carbon monoxide (CO), and the like. In response to the above, the displaying unit 150 may display the analyzed components of air on a screen, and may display the abnormal gas components to be emphasized. When the property of the components of air is an abnormal gas component, the electronic device may display the name and the ratio of the abnormal gas component to be emphasized by using a color and a size.

Also, the electronic device may obtain an image using the camera 120, the processing unit 160 may recognize image information obtained by the camera, and may analyze detected components of air based on the recognized image information, and the displaying unit 150 may display the analyzed components of air in the displayed image.

Also, the processing unit 160 may analyze whether an abnormal gas component exists in the analyzed components of air, and the displaying unit 150 may display the analyzed components of air in the displayed image, and may display the abnormal gas component to be emphasized.

The processing unit 160 may include an object recognizing module 230 that recognizes an object from an image, the analyzing module 210 that analyzes the components of air associated with the recognized object, and the display control module 250 that displays the object image in the display unit, and displays the analyzed components of air in the displayed object image.

Also, the processing unit 160 may include the object recognizing module 230 that recognizes an object from an image, the direction control module 220 that controls a direction of the gas sensor 110 to correspond to the image, the analyzing module 210 that analyzes gases associated with the recognized object, from the gases detected by the gas sensor, and the display control module 250 that displays the object image in the display unit 150 and displays the analyzed components of air in the displayed object image.

Also, the processing unit 160 may include the character recognizing module 240 that recognizes a character from an image, the analyzing module 210 that analyzes components of air associated with the recognized character from the components of air detected by the gas sensor 110, and the display control module 250 that displays an image in the displaying unit 150 and displays the analyzed gases in the displayed image.

Also, the electronic device may further include the communication unit 170. The processing unit 160 may include a module that recognizes a logo and/or label information of a product from an image, the analyzing module 210 that analyzes gases associated with the recognized information from the gases detected by the gas sensor 110, a communication module that communicates the recognized product information according to the controlled direction of the gas sensor 110 with an external device through the communication unit 170, and the display control module 250 that displays an image in the displaying unit 150, and displays the analyzed gases and the communication information in the displayed image.

An electronic device according to various embodiments of the present disclosure may be equipped with the gas sensor 110, so as to detect and display gases. The electronic device may execute the methods as follows.

While operating the gas sensor 110 and the preview of the camera 120, the electronic device may obtain a gas collecting direction and an image, and the electronic device may analyze the collected image and display the same in various forms. For example, the electronic device aims the camera 120 at a gas range, and may measure, using the gas sensor 110, the components of gases that are being oxidized. The electronic device analyzes a component ratio (percentage) of the measured gases, and may display a result thereof in the display unit 150, as AR in different sizes according to a corresponding component ratio. Also, when an abnormal gas (e.g., CO) exists in the analyzed gases, the electronic device may display the same to be emphasized. When a component ratio of the abnormal gas is greater than a reference value, the electronic device may display the same in the display unit 150 to call the attention of the user.

The electronic device may drive the gas sensor 110 and the preview of the camera 120 to interoperate with each other, and may recognize an object in an image obtained by the camera (Optical Object Recognition (OOR)). The electronic device collects gas by setting a collecting direction of the gas sensor to a photographing direction of the camera, and gases that may be detected from the recognized object and related information may be obtained from an external server through the storage unit 130 or the communication unit 170. For example, when the recognized object is a bed, the electronic device may collect an image of a bed that is obtained from the camera 120, elements (e.g., components of fabrics) that may be obtained from an external server or the like, and components of gases collected through the gas sensor 110. The electronic device may analyze the collected information and may determine whether a harmful substance is detected from a piece of new furniture (bed). When harmful gas is detected, the electronic device displays a warning in the display unit 150, and induces the user to remove or cope with a causative substance.

The electronic device may drive the gas sensor 110 and the preview of the camera 120 to interoperate with each other, and may recognize a character included in an image obtained by the camera 120 (Optical Character Recognition (OCR)). The electronic device collects gas by setting a collecting direction of the gas sensor 110 to a photographing direction of the camera 120, and may obtain gases that may be detected from the recognized character and related information through the storage unit 130 and/or an external server (that is connected through the communication unit 170). For example, when the recognized character is 'perfume', the electronic device may collect characters obtained by the camera 120 (e.g., a brand name), information associated with the perfume obtained from the storage unit 130 and/or the external server, and gases collected through the gas sensor 110. The electronic device may provide information associated with the brand name of the perfume that a user desires to know, by analyzing the collected information, and may spray and/or share a sample using an accessory.

Figure 3:
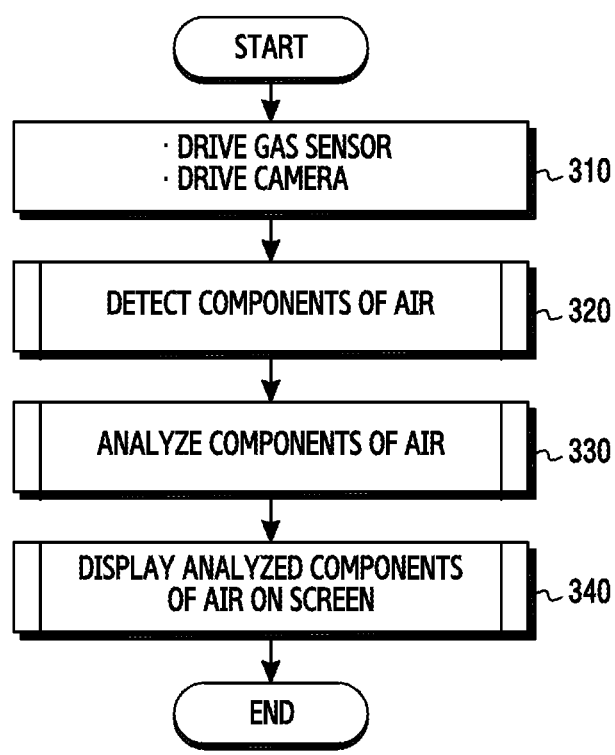
FIG. 3 is a flowchart illustrating example operations of an electronic device to detect gas according to various embodiments of the present disclosure.

FIG. 3 is a flowchart illustrating example operations of an electronic device to detect gas according to various embodiments of the present disclosure. The operation procedure of FIG. 3 may be controlled by the configured processing circuitry of the processing unit 160 of FIG. 1.

Referring to FIG. 3, when an input that requires the execution of detecting gas and the execution of a camera is detected, the electronic device may operate the gas sensor 110 and the camera 120 in operation 310. The request for executing the detection of gas and for executing the camera may be manually provided from a user, or may be provided automatically according to a method that is set in advance in the electronic device 100. When the gas sensor 110 and the camera 120 are driven in operation 310, the electronic device may detect gas existing around the electronic device by using the gas sensor 110 in operation 320.

The electronic device analyzes the gases detected by the gas sensor 110, in operation 330. When the electronic device analyzes the gas, the electronic device may include an operation of analyzing names, types, a component ratio, and the like in association with the detected gases. The gas sensor 110 may be selected based on the purpose of use. For example, the gas sensor 110 may detect a gas leak in a house, may detect gas that is dangerous to the human body from the air, or may detect harmful gas (formaldehyde, acetone, toluene, radon, and the like) that causes Sick House syndrome. Also, the gas sensor 110 may detect gas that is generated from a predetermined product (e.g., an aromatic product such as perfume, a product that generates a predetermined harmful gas such as furniture, and the like).

The electronic device displays the gases detected by the gas sensor 110 on a screen of the electronic device, for example, in real time, in operation 340. Here, the screen of the electronic device may be a preview screen of the camera 120. Also, the electronic device may display the names, the types, the component ratio, and the like, in association with the detected gases, in operation 340. Also, the electronic device may display the names and/or the types of the gases by using characters, in operation 340. Also, the electronic device may display the component ratio of the gases as figures based on a relative size, in operation 340.

Figure 4:
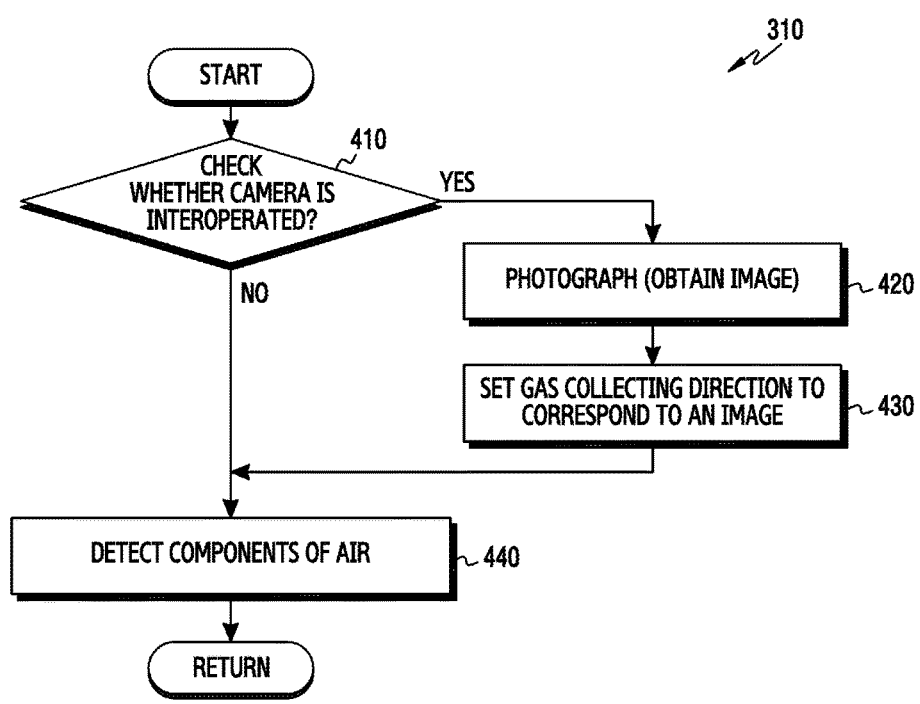
FIG. 4 is a flowchart illustrating example operations of an electronic device to detect gases by interoperating with a camera according to various embodiments of the present disclosure.

FIG. 4 is a flowchart illustrating example operations of an electronic device to detect gases by interoperating with a camera according to various embodiments of the present disclosure. In FIG. 4, the electronic device may detect gas by interoperating with the operations of a camera. The operation procedure of FIG. 4 may be controlled by the configured processing circuitry of the processing unit 160 of FIG. 1. FIG. 4 may correspond to operation 320 of FIG. 3.

Referring to FIG. 4, when the gas sensor 110 is driven, the electronic device checks whether the gas sensor 110 and the camera 120 interoperate with each other, in operation 410. When the interoperation with the camera is set, the gas sensor 110 may set a gas detecting direction to a photographing direction of the camera 120, so as to detect the components of air. Also, the gas sensor 110 may be set to operate independently from the operations of the camera 120. According to an embodiment of the present disclosure, when the camera 120 is driven, the gas sensor 110 may set the gas detecting direction to the photographing direction of the camera 120, and may detect the components of air.

In the case of the interoperation with the camera, the electronic device may respectively operate the gas sensor 110 and the camera 120. In this instance, when the camera 120 is operated, the electronic device may check whether the gas sensor 110 is set to interoperate with the camera 120 in operation 410. In this instance, when the gas sensor is set to interoperate with the camera 120, the electronic device obtains an image photographed by the camera 120 in operation 420, and sets the gas detecting direction of the gas sensor 110 to correspond to a photographing direction of the camera 120 in operation 430.

Subsequently, the electronic device detects the components of air collected by the gas sensor 110 in operation 440. When it is determined that the interoperation with the camera 120 is not set, the electronic device may detect the components of air collected by the gas sensor 110 in operation 440. In this instance, the collecting direction of the gas sensor 110 may not have directionality, and may collect the components of air existing in all directions around the electronic device.

When the camera 120 and the gas sensor 110 interoperate with each other, the electronic device may provide a user with a visual reference in association with a part where the components of air are to be detected. The electronic device may set a collecting direction of the gas sensor 110 to correspond to the image obtained by the camera 120. As described above, when the collecting direction of the gas sensor 110 is set, the electronic device may intensively detect the components of air that are generated from a predetermined object or the like. For example, when the collecting direction is set through interoperating with the camera 120, the electronic device may obtain an image corresponding to a target object of the collection of the components of air, and may collect the components of air generated from the corresponding object. When the interoperation with the camera 120 is not set (that is, when it is determined that the gas sensor 110 and the camera 120 do not interoperate in operation 410), the gas sensor 110 may detect the components of air in all the directions around the electronic device. In this instance, the user may obtain information associated with the components of a broad range of air around the electronic device. In this instance, a method of setting the direction of the gas sensor 110 that corresponds to the obtained image may include: an operation of activating a gas sensor that is adjacent to the camera 120; an operation of aiming the gas sensor at the direction of the obtained image; or an operation executed by a combination thereof.

Figure 5:
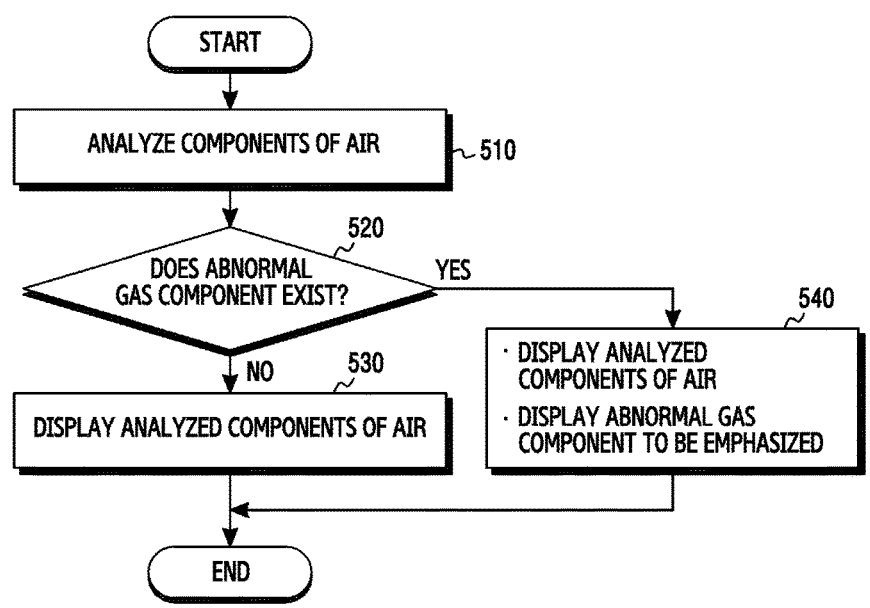
FIG. 5 is a flowchart illustrating example operations of an electronic device when an abnormal gas component exists according to various embodiments of the present disclosure.

FIG. 5 is a flowchart illustrating example operations of an electronic device for detecting the components of air when an abnormal gas component exists according to various embodiments of the present disclosure. The operation procedure of FIG. 5 may be controlled by the configured processing circuitry of the processing unit 160 of FIG. 1. The embodiment illustrated in FIG. 5 may correspond to operation 330 of FIG. 3.

Referring to FIG. 5, the electronic device analyzes the components of air detected by the gas sensor 110 in operation 510. In operation 510, the electronic device may analyze names, types, and the like in association with the detected components of air, in the same manner as operation 330.

Subsequently, the electronic device analyzes whether an abnormal gas component is included in the analyzed components of air in operation 520. When an extremely small amount of gas that is harmful to the human body (e.g., potassium cyanide, arsenic trioxide, carbon monoxide, sulfur dioxide, hydrogen chloride, or the like) is included in the components of air analyzed in operation 510, the electronic device may determine the gas as an abnormal gas component. Also, the electronic device may determine whether an abnormal gas component exists in the components of air by taking into consideration the concentration of the gas analyzed in operation 520. That is, when an excessively large amount of a component of air or a relatively small amount of a component of air is detected while the concentration of the components of air is analyzed, the component may be determined as an abnormal gas component. For example, when an excessive amount of nitrogen exists in a closed room or an excessively small amount of oxygen exists in a closed room, the electronic device may determine that nitrogen or oxygen in the analyzed components of air may be determined as an abnormal gas component.

As described above, after analyzing the types and the concentration of the components of air and whether an abnormal gas component exists, the electronic device may display, in the display unit 150, information differently based on whether an abnormal gas component is included. When it is determined that the abnormal gas component is not included in the analyzed components of air, the electronic device displays the analyzed gases in the display unit 150, in operation 530. However, when it is determined that the abnormal gas component is included in the analyzed components of air, the electronic device displays the analyzed components of air in the display unit 150, and may display the abnormal gas component to be emphasized in operation 540. In this instance, the names of the components of air analyzed in operations 520 and 530 may be displayed in different sizes (and/or colors) based on a corresponding concentration (component ratio). Also, the components of air may be displayed in the form of Augmented Reality (AR) together with an image.

For example, when an abnormal gas component is not included in the detected components of air, the electronic device may display the detected components of air based on a corresponding concentration. Also, the electronic device may display the analyzed components of air in the display unit 150, based on a corresponding ratio. Also, the electronic device may display the ratio of the detected gases in the display unit 150, through characters based on a scheme designated by a user (e.g., % ratio, mole ratio, molar ratio, mass, volume, and the like). Also, the electronic device may display the ratio of the detected gases in the display unit 150, through figures based on a scheme designated by a user (e.g., a stick, a straight line, a curve, a circle, a square, a triangle, and the like). Also, the electronic device may display, in the display unit 150, the ratio of the detected gases by combining the characters and figures.

When abnormal gas components exist in the detected gases, the electronic device displays the detected components of air and the abnormal gas components in operation 540. In this instance, the electronic device may display, in the display unit 150, the detected components of air as in operation 530, and may display the abnormal gas components to be emphasized when compared to the other detected components of air. Also, when the property of the analyzed component of air is an abnormal gas component, the electronic device may display the name and the ratio of the abnormal gas component to be emphasized.

Figure 6:
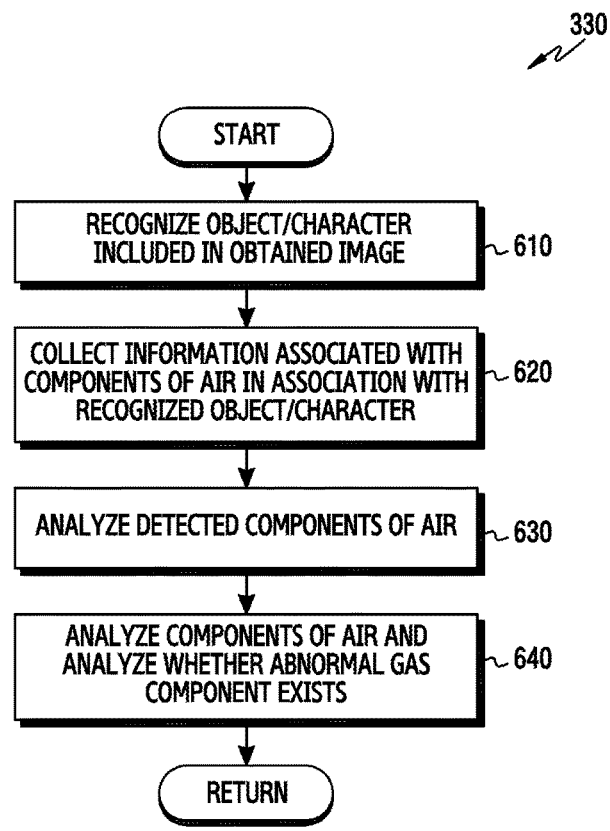
FIG. 6 is a flowchart illustrating an example method in which an electronic device analyzes detected gas according to various embodiments of the present disclosure.

FIG. 6 is a flowchart illustrating an example method in which an electronic device analyzes detected gas according to various embodiments of the present disclosure. FIG. 6 illustrates a method of analyzing gas when gas is detected by interoperating with a camera. The operation procedure of FIG. 6 may be controlled by the configured processing circuitry of the processing unit 160 of FIG. 1.

Referring to FIG. 6, when an image is obtained through the camera 120, the electronic device extracts image information through the image in operation 610. For example, the image information may be an object or a character included in the image.

The electronic device may extract gas information associated with the image information in operation 620. For example, the gas information associated with the object or character included in the image may be extracted. The gas information of the object or the character may require reference data. When the reference data is stored in the storage unit 130, the electronic device may collect additional information associated with the object or the character, using the reference data in the storage unit 130. When the reference data is not stored in the storage unit 130, the electronic device may collect information associated with the object or the character from an external server through the communication unit 170. For example, when the electronic device obtains an image including a combusting cigarette and/or a label of a cigarette in operation 610, the electronic device may collect gas information associated with gas (e.g., nicotine, tar, carbon monoxide, carbon dioxide, and the like) that is normally discharged from a cigarette, based on the cigarette (extracted object), in operation 620. Also, the electronic device may specify the type of the cigarette through the label of the cigarette (the extracted character), and may collect the gas information associated with gas that is normally discharged from the specified cigarette in operation 620. The electronic device analyzes the gases detected by the gas sensor 110, in operation 630. The operation procedure of operation 630 may correspond to operation 330 of FIG. 3. The electronic device analyzes the gases detected by the gas sensor 110, in operation 630. The electronic device may include an operation of analyzing names, types, or a component ratio of the detected gases, or whether abnormal gas exists.

Operations 620 and 630 may be processed in reverse order in the electronic device, unlike the embodiment of FIG. 6, or may be processed in parallel.

The electronic device processes gas information associated with the object or the character, in operation 640. The electronic device may determine the types or the component ratio of the gases discharged from the object, whether abnormal gases are included, or the like in operation 640. The electronic device may specify the types and the component ratio of the gases based on a result of the analysis of operation 620. Subsequently, the electronic device may analyze whether abnormal gas exists based on the result of the analysis.

Figure 7:
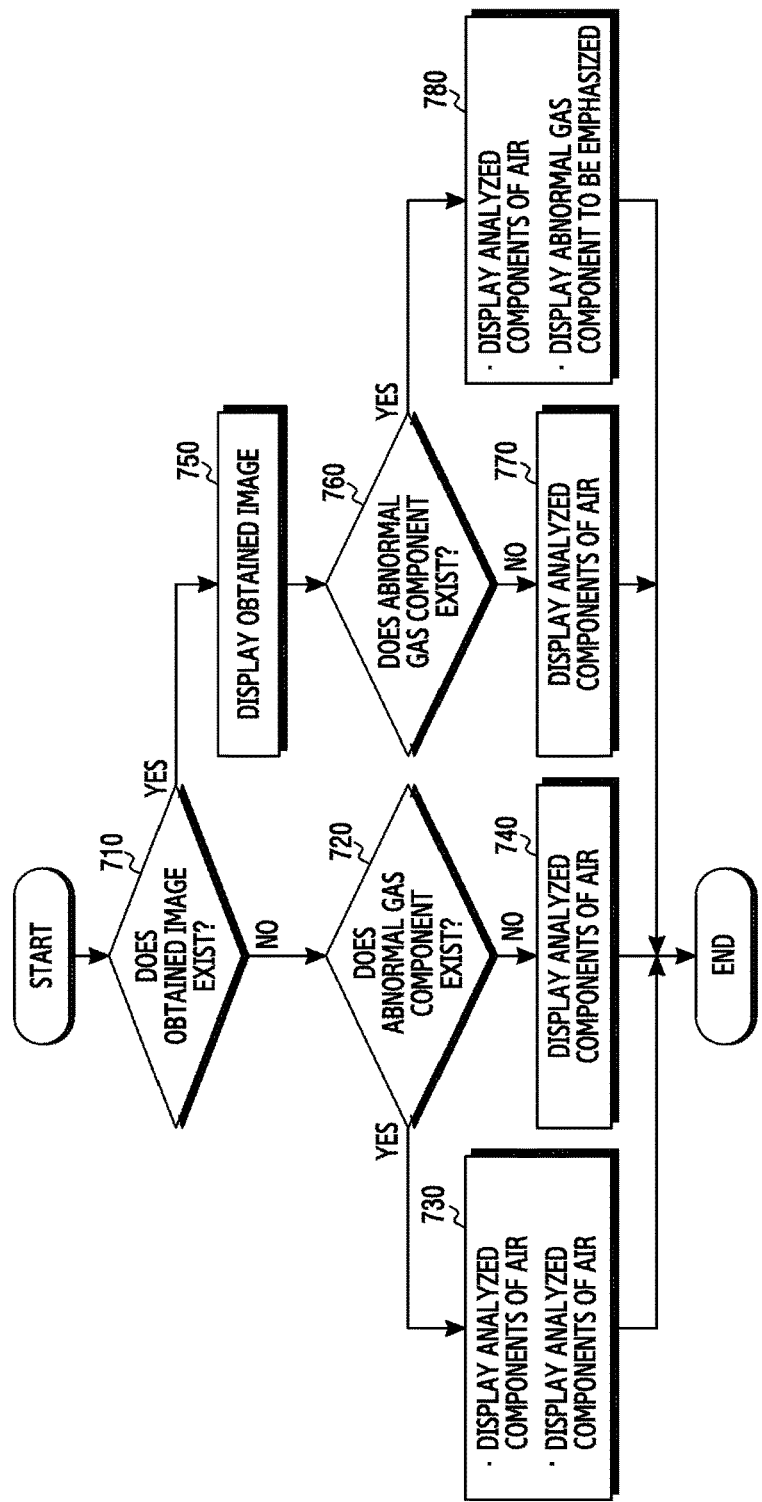
FIG. 7 is a flowchart illustrating example operations of an electronic device that displays detected gas according to various embodiments of the present disclosure.

FIG. 7 is a flowchart illustrating example operations of an electronic device that displays detected gas according to various embodiments of the present disclosure. The operation procedure of FIG. 7 may be controlled by the configured processing circuitry of the processing unit 160 of FIG. 1. Also, the operation procedure of FIG. 7 may be displayed in the display unit 150 of FIG. 1.

Referring to FIG. 7, when the analysis of the gases detected through the gas sensor is completed, the electronic device displays, in the display unit 150, the gases differently based on whether an obtained image exists in operation 710. That is, in operation 710, the electronic device may display the gases differently based on whether a camera is interoperated, or may display the gases differently based on whether an obtained image exists when the camera is interoperated.

When the obtained image does not exist, the electronic device checks whether abnormal gas exists in operation 720. When the abnormal gas does not exist, the electronic device displays the analyzed gases in operation 740. Conversely, when the abnormal gas exists, the electronic device displays the analyzed gases, and displays the abnormal gases to be emphasized, in operation 730. Operations 730 and 740 may correspond to operations 530 and 540 illustrated in FIG. 5.

Unlike the above, when the obtained image exists, the electronic device displays the obtained image in the display unit 150 in operation 750. Subsequently, the electronic device may check whether abnormal gas exists in operation 760.

When the abnormal gas does not exist, the electronic device may display the analyzed gases to overlap the obtained image in operation 770. The electronic device may display the types or the component ratio of the analyzed gases in the display unit 150, and may display, in the image, gas information (e.g., name and/or component ratio or the like) corresponding to the location where the gases are generated. Therefore, users may determine, from the information in the display unit 150, the name and/or the component ratio of the detected gas, and the location where the gas is generated, and the like. In this instance, the analyzed gases may be displayed by the method used in operation 530.

When abnormal gas exists, the electronic device determines the same in operation 760, and displays the names, the component ratio, and the like of the analyzed gases in the obtained image and displays the abnormal gases to be emphasized, in operation 780. In this instance, the user may determine the types or the component ratio of the analyzed gases, and may determine the types or the component ratio of the abnormal gases displayed to be emphasized, through the display unit 150. When the abnormal gas is detected, a warning message may be displayed through the display unit 150. In this instance, the analyzed gases and the abnormal gases may be displayed by the method as described in operation 540.

As described above, when the gas is detected and displayed, the electronic device according to an embodiment of the present disclosure may drive the gas sensor 110 to interoperate with a camera, or may drive only the gas sensor 110. Operations 750 to 780 of FIG. 7 illustrate an example of analyzing an obtained image and detected gas in the state in which the gas sensor 110 and the camera 120 interoperate with each other. Operations 720 to 740 illustrate an example of analyzing only the gas detected by the gas sensor. When only the gas sensor 110 is driven, the electronic device may collect gas through the gas sensor 110, may analyze the names and the component ratio of the collected gases, and may display the same in the display unit 150. In this instance, the method of displaying the gases may display the gases to overlap an image set in the display unit 150, or may display only gas information.

Figure 8:
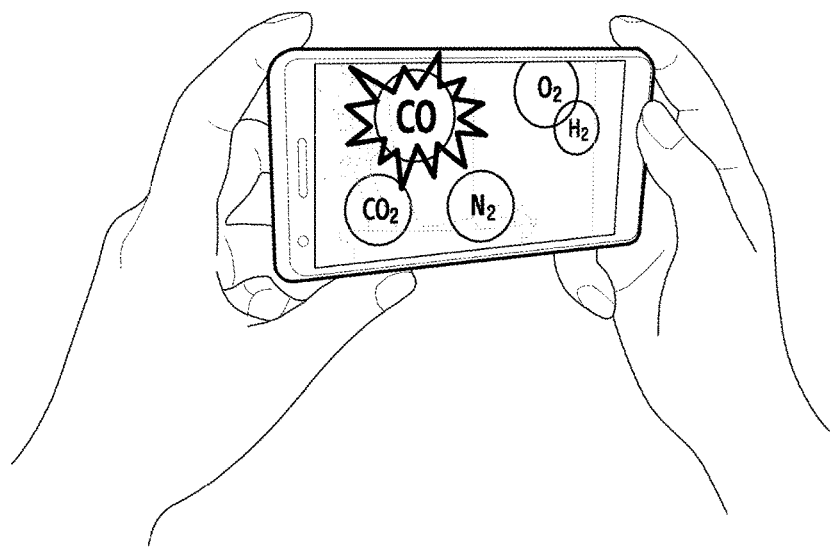
FIG. 8 is a diagram illustrating an example in which an electronic device displays detected gas according to various embodiments of the present disclosure.
Figure 9:
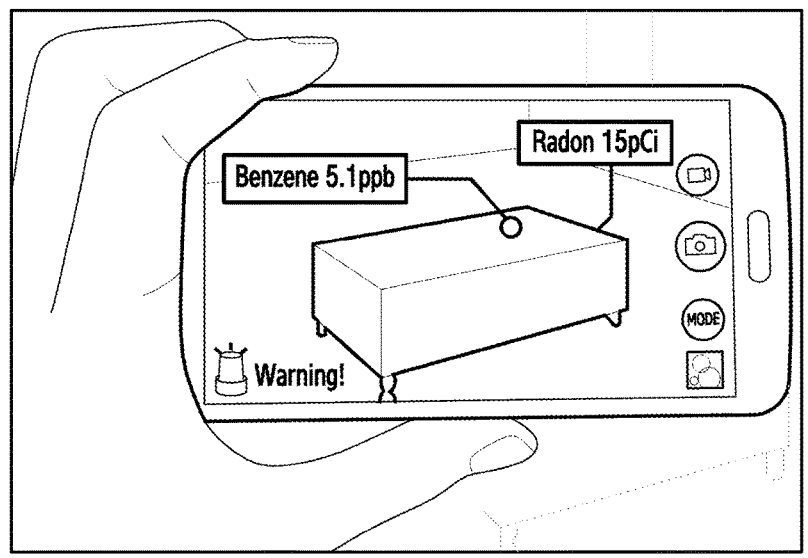
FIG. 9 is a diagram illustrating an example in which an electronic device displays detected gas to overlap a photographed image according to various embodiments of the present disclosure.

FIG. 8 is a diagram illustrating an example in which an electronic device displays detected gas according to various embodiments of the present disclosure. FIG. 9 is a diagram illustrating an example in which an electronic device displays detected gas to overlap a photographed image according to various embodiments of the present disclosure. FIGS. 8 and 9 illustrate an example in which abnormal gas is included in analyzed gas. FIG. 8 is a displaying method in operation 540 of FIG. 5 or operation 730 of FIG. 7 FIG. 9 may be a displaying method in operation 780 of FIG. 7.

FIG. 8 illustrates an example of displaying names and a component ratio of analyzed gases (nitrogen ($N_2$), hydrogen ($H_2$), oxygen ($O_2$), carbon dioxide ($CO_2$), and carbon monoxide (CO)). In this instance, the image displayed in the displaying unit 150 may be an image that is not associated with the gases, or no image may be displayed. Also, the electronic device may display the size (area) of a figure (circle) to correspond to a component ratio of gas in FIG. 8. Also, the electronic device displays abnormal gas to be emphasized in FIG. 8. Particularly, the electronic device displays carbon monoxide to be emphasized when compared to other gases in FIG. 8. In FIG. 8, the electronic device determines carbon monoxide as abnormal gas and may control the display unit 150 of the electronic device to display carbon monoxide to be emphasized irrespective of the absolute amount of carbon monoxide.

Referring to FIG. 9, the electronic device displays (Benzene and Radon) the analyzed gases. The electronic device may display an image (e.g., furniture) obtained by the camera 120 in FIG. 9. Also, the electronic device may display the type of the gas (Benzene and Radon) to overlap the obtained image in FIG. 9. Also, the electronic device may display an amount of gas emission through characters (Benzene 5.1 ppb and Radon 15 pCi) in FIG. 9. Also, the electronic device displays abnormal gas to be emphasized in FIG. 9. Particularly, the electronic device may not display other gases discharged from fabrics included in the chair but may display only Benzene and Radon which are abnormal gases, and thus, may display the abnormal gas to be emphasized. Also, the electronic device may provide a warning indicating that a user is in an abnormal situation through a warning figure and characters "warning!" displayed in the left bottom of the screen in FIG. 9. The displaying method of FIG. 9 may be one of the emphasizing methods according to various embodiments of the present disclosure.

Figure 10:
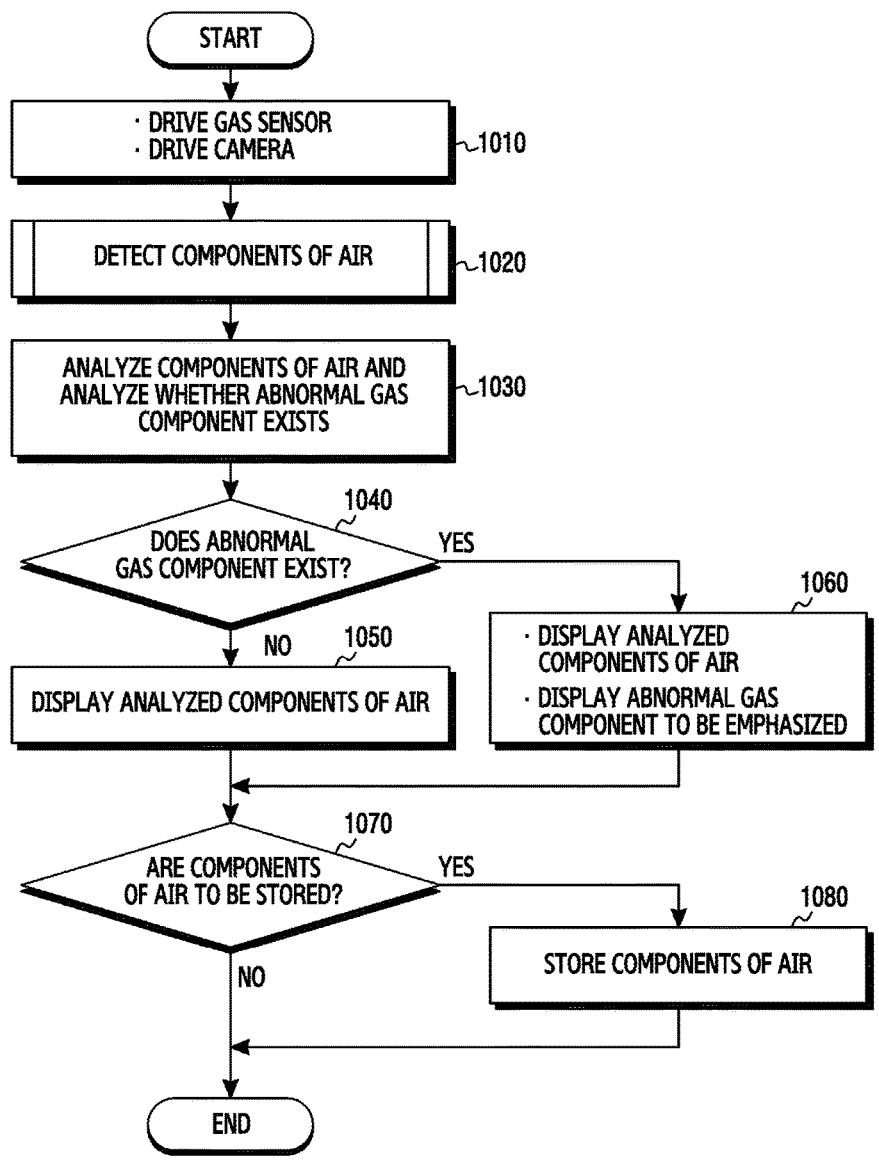
FIG. 10 is a flowchart illustrating an example method in which an electronic device detects gas and displays the same according to various embodiments of the present disclosure.

FIG. 10 is a flowchart illustrating an example method in which an electronic device detects gas according to various embodiments of the present disclosure. The operation procedure of FIG. 10 may be controlled by the configured processing circuitry of the processing unit 160 of FIG. 1.

Referring to FIG. 10, the electronic device may detect gas through the gas sensor 110, may analyze the detected gas so as to determine a component ratio and whether abnormal gas exists, and may display a result thereof in the display unit 150, through performing operations 1010 to 1060.

The electronic device may store, in the gas storage unit 180, gas detected while collecting gas. Also, the gas storage unit 180 may store gas that flows from the outside, under the control of the processing unit 160. For example, a user may store perfume in the electronic device. When a request for storing the perfume exists, the processing unit 160 controls the gas storage unit and stores the gases forming the external perfume. In the state in which the gases are stored, the electronic device displays the names and the component ratio, and the like of the detected gases in operation 1050 or 1060. The electronic device determines whether to store gas in the gas storage unit 180 in operation 1070. When the electronic device determines to store gas, the electronic device stores the gas in the gas storage unit 180 in operation 1080. The gas storage unit 180 may spray the gas stored in operation 1080. For example, when the gas stored in the gas storage unit 180 is identical or similar to the currently collected gas, the electronic device may spray gases stored in the gas storage unit 180 using a cartridge. In this instance, the electronic device may discharge gas formed of the identical components of the detected gases.

Figure 11:
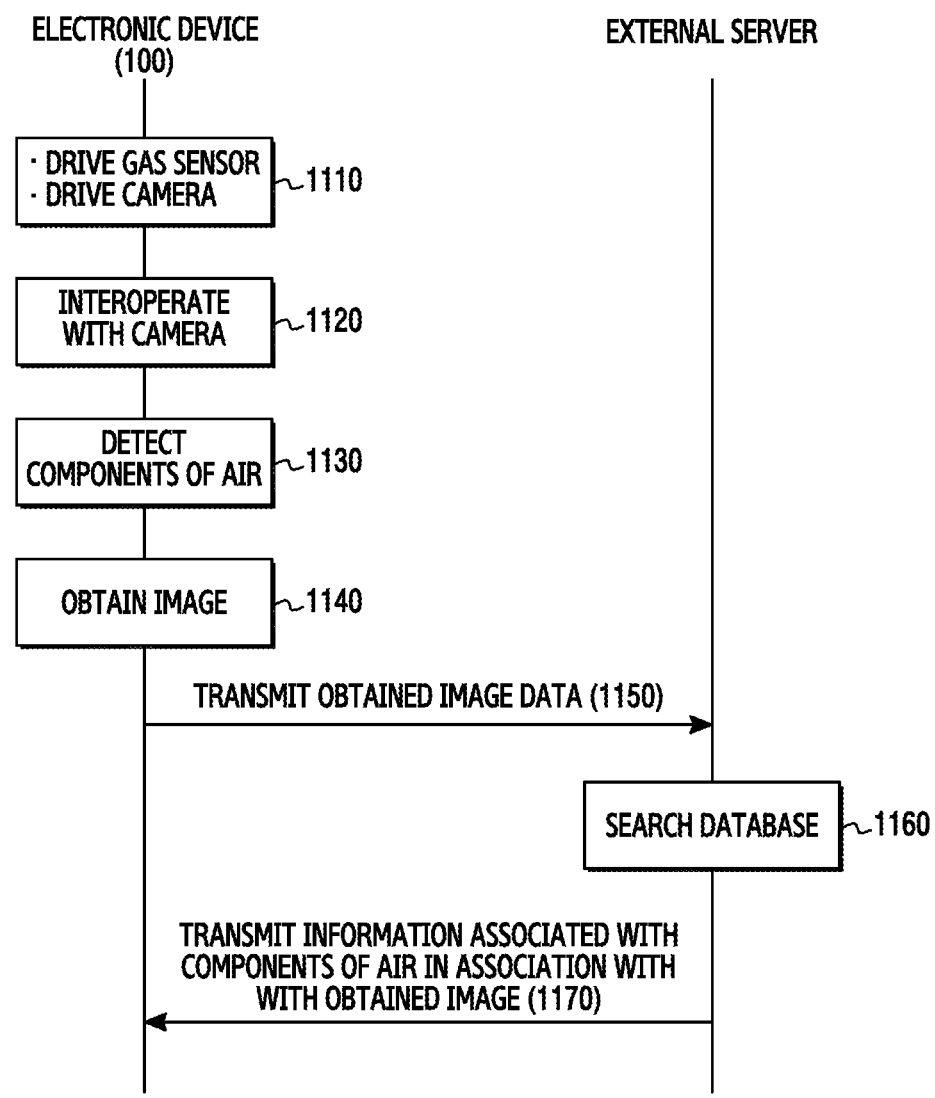
FIG. 11 is a flowchart illustrating example operations of an electronic device that downloads gas information associated with image information, through an external server, according to various embodiments of the present disclosure.

FIG. 11 is a flowchart illustrating example operations of an electronic device that downloads gas information associated with image information, through an external server, according to various embodiments of the present disclosure. The operation procedure of FIG. 11 may be controlled by the configured processing circuitry of processing unit 160 of FIG. 1. The operation procedure of FIG. 11 may exchange data with an external server through the communication unit 170 of FIG. 1.

Referring to FIG. 11, when an input for requesting the execution of detecting gas is detected, the electronic device drives the gas sensor 110 in operation 1110. Subsequently, when interoperation with the camera 120 is determined as the gas sensor 110 is driven, the electronic device interoperates with the camera in operation 1120. Subsequently, the electronic device detects gas using the gas sensor 110 in operation 1130. Operations 1120 and 1130 may be performed in reverse order, or in parallel. Subsequently, the electronic device may obtain an image through the camera 120 in operation 1140. Operation 1140 may correspond to operation 420 of FIG. 4.

The electronic device may transmit the obtained image to an external server through the communication unit 170 in operation 1150. The transmission to the external server may be performed through the communication unit 170 included in the electronic device. The transmission to the external server may be useful when gas information associated with the obtained image information is not obtained from the storage unit 130 or the like included in the electronic device.

The external server, in operation 1160, may search for gas information associated with the image information from a database in the external server, based on the transmitted image information. When the gas information is retrieved from the database, the external server transmits the gas information to the electronic device in operation 1170. The gas information transmitted in operation 1170 may be used by the processing unit 160.

Figure 12:
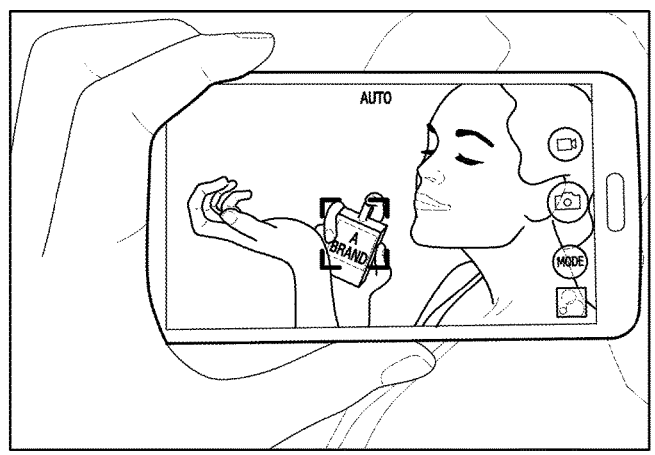
FIG. 12 is a diagram illustrating an example of displaying gas information when an obtained image is a character according to various embodiments of the present disclosure.

FIG. 12 is a diagram illustrating an example of displaying gas information when an obtained image is a character according to various embodiments of the present disclosure.

FIG. 12 illustrates an example of an image photographed by the camera 120 as an image that includes a perfume bottle and the label of the brand name of perfume. Then, the electronic device may recognize an object and/or characters from the image. The electronic device may collect gas information corresponding to the brand A through the recognized characters (the label of brand A). Also, the electronic device may collect gas information corresponding to the perfume bottle through the object (perfume bottle) recognized through the processing unit 160 in FIG. 12. The collected gas information associated with the characters and gas information associated with the perfume bottle may be processed by the processing unit 160 in operation 620. Subsequently, the electronic device may display the analyzed gas (perfume) information through characters, to overlap the obtained image.

An operation method of an electronic device according to various embodiments of the present disclosure may include: driving the gas sensor 110 and the camera 120; detecting components of air using the gas sensor 110; analyzing the detected components of air; and displaying the analyzed components of air on a screen in real time. The electronic device may analyze the component ratio of the detected components of air, and may display the components of air based on the component ratio of the analyzed components of air. The electronic device may further include: analyzing whether an abnormal gas component exists in the analyzed components of air, displaying the analyzed components of air on a screen, and displaying the abnormal gas component to be emphasized. Also, the color and the form of the name of the abnormal gas component may be displayed to be emphasized.

Also, the electronic device may further include: recognizing image information obtained by the camera 120; analyzing the detected components of air based on the recognized image information; and displaying the image and displaying the analyzed components of air in the image. The electronic device may further include: analyzing whether an abnormal gas component exists in the analyzed components of air; displaying the analyzed components of air in the displayed image; and displaying the abnormal gas component to be emphasized. When the image information is object information, the electronic device may perform analyzing the components of air associated with the object from the detected components of air, and may perform displaying the analyzed components of air in the object image. Also, when the image information is object information, the electronic device may control the gas sensor 110 to collect the components of air existing in a photographing direction of the camera 120, and may display the names and the component ratio of the analyzed components of air in the object image. When the image information is character information, the electronic device may analyze the components of air associated with the characters. When the image information is a logo and/or label information of a product, the electronic device may collect additional information of the product through the storage unit 130 and/or the communication unit 170, and may display the analyzed components of air and product information associated with the additional information, in the display unit 150.

Methods stated in claims and/or descriptions according to various embodiments may be implemented by hardware, software, or a combination of hardware and software.

In the implementation of software, a computer-readable storage medium for storing one or more programs (software modules) may be provided. The one or more programs stored in the computer-readable storage medium may be configured for execution by one or more processors within the electronic device. The at least one program may include instructions that cause the electronic device to perform the methods according to various embodiments of the present disclosure as defined by the appended claims and/or disclosed herein.

The programs (software modules or software) may be stored in non-volatile memories including a random access memory and a flash memory, a Read Only Memory (ROM), an Electrically Erasable Programmable Read Only Memory (EEPROM), a magnetic disc storage device, a Compact Disc-ROM (CD-ROM), Digital Versatile Discs (DVDs), or other type optical storage devices, or a magnetic cassette. Alternatively, any combination of some or all of the may form a memory in which the program is stored. Further, a plurality of such memories may be included in the electronic device.

In addition, the programs may be stored in an attachable storage device which may access the electronic device through communication networks such as the Internet, Intranet, Local Area Network (LAN), Wide LAN (WLAN), and Storage Area Network (SAN) or a combination thereof. Such a storage device may access the electronic device via an external port. Further, a separate storage device on the communication network may access a portable electronic device.

In the above-described example embodiments of the present disclosure, a component included in the present disclosure is expressed in the singular or the plural according to a presented example embodiment. However, the singular form or plural form is selected for convenience of description suitable for the presented situation, and various embodiments of the present disclosure are not limited to a single element or multiple elements thereof. Further, either multiple elements expressed in the description may be configured into a single element or a single element in the description may be configured into multiple elements.

Although the various example embodiments have been described in the detailed description of the present disclosure, the present disclosure may be modified in various forms without departing from the scope of the present disclosure. Therefore, the scope of the present disclosure should not be defined as being limited to the disclosed example embodiments, but should be defined by the appended claims and equivalents thereof.

What is claimed is:

1. A method for operating an electronic device, the method comprising:
   detecting components of air using a gas sensor of the electronic device;
   determining whether a particular component, of the detected components, is abnormal based on at least reference data comprising gases normally associated with an object in an image from a camera of the electronic device; and
   displaying information regarding the components of air superimposed on a preview image being acquired through the camera of the electronic device, including displaying any abnormal gas component with greater emphasis than that of a normal gas component.

2. The method of claim 1, furthering comprising:
   identifying a component ratio of the detected components of air,
   wherein displaying the information regarding the components of air comprises displaying, based on a magnitude of the component ratio of the components of air, the information regarding the components of air that is superimposed on the preview image being acquired through the camera of the electronic device.

3. The method of claim 1, wherein the abnormal gas component is highlighted by displaying a color and a form of a name of the abnormal gas component.

4. The method of claim 1, wherein detecting the components of air comprises detecting the components of air located within an area directed by the camera.

5. The method of claim 1, wherein the information regarding the components of air is superimposed on the preview image being acquired, for associating at least one object included in the preview image with the components of air.

6. The method of claim 5, wherein the information regarding the components of air includes data regarding names of the components of air or data regarding a component ratio of the components of air.

7. The method of claim 1, further comprising:
   recognizing at least one object included in the preview image; and
   associating, based on the recognition, the components of air with the at least one object,
   wherein the information regarding the components of air is superimposed on the preview image to indicate the association between the components of air and the at least one object.

8. The method of claim 1, further comprising:
   identifying, among the detected components of air, an abnormal gas component,
   wherein displaying the information regarding the components of air comprises displaying, with the information regarding the components of air, a visual indication for indicating that the abnormal gas component exists.

9. The method of claim 1, further comprising:
   recognizing at least one character included in the preview image;
   obtaining information regarding the at least one character, based on a signaling between the electronic device and an external electronic device; and
   analyzing the components of air, based on the information regarding the at least one character,
   wherein displaying the information regarding the components of air comprises displaying, based on a result of the analysis, the information regarding the components of air that is superimposed on the preview image.

10. An electronic device, the device comprising:
a display;
a gas sensor;
a camera; and
a processor configured to:
  detect components of air using the gas sensor;
  determine whether a particular component, of the detected components, is abnormal based on at least reference data comprising gases normally associated with an object in an image from the camera of the electronic device; and
  display, by using the display, information regarding the components of air that is superimposed on a preview image being acquired through the camera, including display any abnormal gas component with greater emphasis than that of a normal gas component.

11. The device of claim 10, wherein the processor is further configured to:
  identify a component ratio of the detected components of air,
  wherein the processor is configured to display, based on a magnitude of the component ratio of the components of air, the information regarding the components of air that is superimposed on the preview image being acquired through the camera.

12. The device of claim 10, wherein the abnormal gas component is highlighted by displaying a color and a form a name of the abnormal gas component.

13. The device of claim 10, wherein the processor is configured to detect the components of air located within an area directed by the camera.

14. The device of claim 13, wherein the information regarding the components of air is superimposed on the preview image being acquired, for associating at least one object included in the preview image with the components of air.

15. The device of claim 14, wherein the information regarding the components of air includes data regarding names of the components of air or data regarding a component ratio of the components of air.

16. The device of claim 14, wherein the processor is further configured to:
  recognize at least one object included in the preview image; and
  associate, based on the recognition, the components of air with the at least one object, and
  wherein the information regarding the components of air is superimposed on the preview image to indicate the association between the components of air and the at least one object.

17. The device of claim 10, wherein the processor is further configured to identify, among the detected components of air, an abnormal gas component, and
  wherein the processor is configured to display, with the information regarding the components of air, a visual indication for indicating that the abnormal gas component exists.

18. The device of claim 10, wherein the processor is further configured to:
  recognize at least one character included in the preview image;
  obtain information regarding the at least one character, based on a signaling between the electronic device and an external electronic device; and
  analyze the components of air, based on the information regarding the at least one character, and
  wherein the process is configured to display, based on a result of the analysis, the information regarding the components of air that is superimposed on the preview image.

* * * * *